US008459446B2

United States Patent
Kozlowski

(10) Patent No.: US 8,459,446 B2
(45) Date of Patent: Jun. 11, 2013

(54) SUTURE PACKAGING AND METHODS RELATED THERETO

(75) Inventor: Martin J. Kozlowski, Kutztown, PA (US)

(73) Assignee: Ethicon, Inc., Somerville, NJ (US)

( * ) Notice: Subject to any disclaimer, the term of this patent is extended or adjusted under 35 U.S.C. 154(b) by 119 days.

(21) Appl. No.: 12/677,505

(22) PCT Filed: Sep. 10, 2008

(86) PCT No.: PCT/US2008/075849
§ 371 (c)(1),
(2), (4) Date: Nov. 19, 2010

(87) PCT Pub. No.: WO2009/036060
PCT Pub. Date: Mar. 19, 2009

(65) Prior Publication Data
US 2011/0056859 A1    Mar. 10, 2011

Related U.S. Application Data

(60) Provisional application No. 60/971,135, filed on Sep. 10, 2007.

(51) Int. Cl.
  *A61B 17/06* (2006.01)
(52) U.S. Cl.
  USPC .................. 206/63.3; 206/227; 53/430
(58) Field of Classification Search
  USPC ............ 206/63.3, 227, 380, 388, 49; 53/429,
                                     53/430, 491; 606/228
  See application file for complete search history.

(56) References Cited

U.S. PATENT DOCUMENTS

| 3,206,018 | A |   | 9/1965  | Lewis et al.    |         |
|-----------|---|---|---------|-----------------|---------|
| 3,545,608 | A |   | 12/1970 | Berger et al.   |         |
| 3,951,261 | A |   | 4/1976  | Mandel et al.   |         |
| 3,981,307 | A |   | 9/1976  | Borysko         |         |
| 3,985,227 | A |   | 10/1976 | Thyen et al.    |         |
| 4,063,638 | A |   | 12/1977 | Marwood         |         |
| 4,135,623 | A | * | 1/1979  | Thyen           | 206/63.3 |
| 4,183,431 | A |   | 1/1980  | Schmidt et al.  |         |
| 4,253,563 | A |   | 3/1981  | Komarnycky      |         |
| 4,813,537 | A | * | 3/1989  | Okuhara et al.  | 206/63.5 |
| 4,946,043 | A | * | 8/1990  | Roshdy et al.   | 206/63.3 |

(Continued)

FOREIGN PATENT DOCUMENTS

| DE | 2618662 | * 11/1977 |
| EP | 1075843 |   2/2005  |

(Continued)

OTHER PUBLICATIONS

International Search Report issued on corresponding PCT Application No. PCT/US2008/075849, dated Jun. 23, 2009.

(Continued)

*Primary Examiner* — David Fidei
(74) *Attorney, Agent, or Firm* — Jon A. Chiodo

(57) ABSTRACT

Suture packaging and methods of use related thereto, wherein sutures are stored in suture packaging (100) having a panel (102) with apertures (104), needle parks (106, 500) removably or fixedly and selectively inserted into the apertures, and wrapping pegs (108, 400) removably or fixedly and selectively inserted into the apertures. The suture package can further comprise a tab (716) and a tab slot (718) for closing the package.

14 Claims, 12 Drawing Sheets

U.S. PATENT DOCUMENTS

| | | | |
|---|---|---|---|
| 5,084,063 A | 1/1992 | Korthoff | |
| 5,102,418 A | 4/1992 | Granger et al. | |
| 5,121,836 A | 6/1992 | Brown et al. | |
| 5,123,911 A | 6/1992 | Granger et al. | |
| 5,131,534 A | 7/1992 | Brown et al. | |
| 5,154,283 A | 10/1992 | Brown | |
| 5,156,615 A | 10/1992 | Korthoff et al. | |
| 5,197,597 A | 3/1993 | Leary et al. | |
| 5,249,673 A | 10/1993 | Sinn | |
| 5,306,288 A | 4/1994 | Granger et al. | |
| 5,312,422 A | 5/1994 | Trott | |
| 5,374,268 A | 12/1994 | Sander | |
| 5,386,912 A | 2/1995 | Holzwarth et al. | |
| 5,425,746 A | 6/1995 | Proto et al. | |
| 5,437,362 A * | 8/1995 | Sinn | 206/63.3 |
| 5,460,263 A | 10/1995 | Brown et al. | |
| 5,464,422 A | 11/1995 | Silverman | |
| 5,494,154 A * | 2/1996 | Ainsworth et al. | 206/63.3 |
| 5,500,991 A | 3/1996 | Demarest et al. | |
| 5,503,266 A * | 4/1996 | Kalbfeld et al. | 206/63.3 |
| 5,533,611 A * | 7/1996 | Bordighon et al. | 206/63.3 |
| 5,566,821 A * | 10/1996 | Brown et al. | 206/63.3 |
| 5,566,822 A | 10/1996 | Scanlon | |
| 5,584,859 A | 12/1996 | Brotz | |
| 5,676,675 A | 10/1997 | Grice | |
| 5,693,072 A | 12/1997 | McIntosh | |
| 5,715,942 A * | 2/1998 | Li et al. | 206/339 |
| 5,722,991 A | 3/1998 | Colligan | |
| 5,871,089 A * | 2/1999 | Odermatt | 206/63.3 |
| 5,897,572 A | 4/1999 | Schulsinger et al. | |
| 5,918,733 A | 7/1999 | Cerwin et al. | |
| 5,931,855 A | 8/1999 | Buncke | |
| 5,941,899 A | 8/1999 | Granger et al. | |
| 6,012,216 A | 1/2000 | Esteves et al. | |
| 6,015,042 A * | 1/2000 | Cerwin et al. | 206/63.3 |
| 6,029,806 A * | 2/2000 | Cerwin et al. | 206/63.3 |
| 6,129,741 A | 10/2000 | Wurster et al. | |
| 6,163,948 A | 12/2000 | Esteves et al. | |
| 6,214,030 B1 | 4/2001 | Matsutani et al. | |
| 6,241,747 B1 | 6/2001 | Ruff | |
| 6,254,616 B1 | 7/2001 | Wright | |
| 6,260,696 B1 | 7/2001 | Braginsky et al. | |
| 6,264,675 B1 | 7/2001 | Brotz | |
| 6,322,581 B1 | 11/2001 | Fukuda et al. | |
| 6,481,569 B1 * | 11/2002 | Alpern | 206/63.3 |
| 6,659,270 B2 * | 12/2003 | Williamson et al. | 206/63.3 |
| 6,739,450 B2 | 5/2004 | Roshdy et al. | |
| 6,848,152 B2 | 2/2005 | Genova et al. | |
| 6,938,755 B2 | 9/2005 | Braginsky et al. | |
| 6,986,780 B2 | 1/2006 | Rudnick et al. | |
| 7,063,716 B2 | 6/2006 | Cunningham | |
| 7,125,403 B2 | 10/2006 | Julian et al. | |
| 7,600,634 B2 * | 10/2009 | Malinowski et al. | 206/63.3 |
| 7,645,293 B2 | 1/2010 | Martinek et al. | |
| 2002/0161168 A1 | 10/2002 | Shalaby et al. | |
| 2003/0052028 A1 * | 3/2003 | Lei | 206/388 |
| 2003/0204193 A1 | 10/2003 | Gabriel et al. | |
| 2003/0204195 A1 | 10/2003 | Keane et al. | |
| 2004/0024169 A1 | 2/2004 | Shalaby et al. | |
| 2004/0050721 A1 | 3/2004 | Roby et al. | |
| 2004/0088003 A1 | 5/2004 | Leung et al. | |
| 2004/0116620 A1 | 6/2004 | Shalaby et al. | |
| 2008/0128296 A1 | 6/2008 | Stopek et al. | |
| 2010/0170812 A1 * | 7/2010 | Odierno | 206/63.3 |

FOREIGN PATENT DOCUMENTS

| | | |
|---|---|---|
| GB | 267007 | 3/1927 |
| JP | 63288146 | 11/1988 |
| WO | WO 2007/053812 | 5/2007 |
| WO | WO 2008/150773 | 12/2008 |
| WO | WO 2009/151876 | 12/2009 |

OTHER PUBLICATIONS

U.S. Appl. No. 09/943,733, filed Aug. 31, 2001.
U.S. Appl. No. 10/065,280, filed Sep. 30, 2002.
U.S. Appl. No. 10/420,993, filed Apr. 22, 2003.
International Preliminary Report on Patentability re: PCT/US2008/064921 dated Dec. 1, 2009.
International Preliminary Report on Patentability re: PCT/US2008/0075849 dated Mar. 16, 2010.
International Preliminary Report on Patentability re: PCT/US2011/040014 dated Dec. 14, 2012.
International Search Report re: PCT/US2008/064921 dated Nov. 19, 2008.
International Search Report re: PCT/US2008/0075849 dated Jun. 23, 2009.
International Search Report re: PCT/US2011/040014 dated Feb. 9, 2012.

* cited by examiner

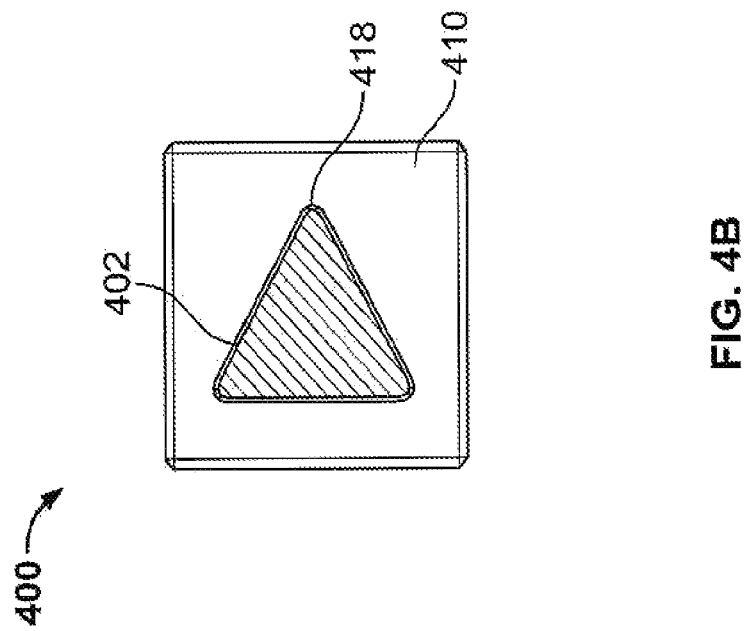
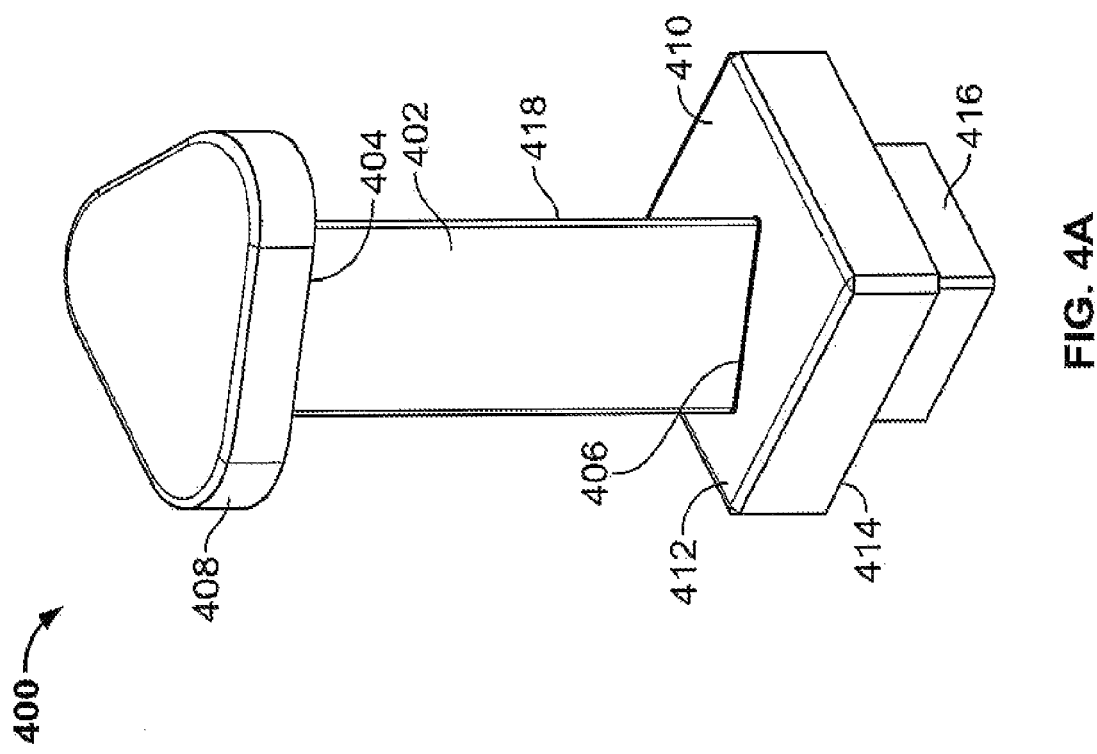

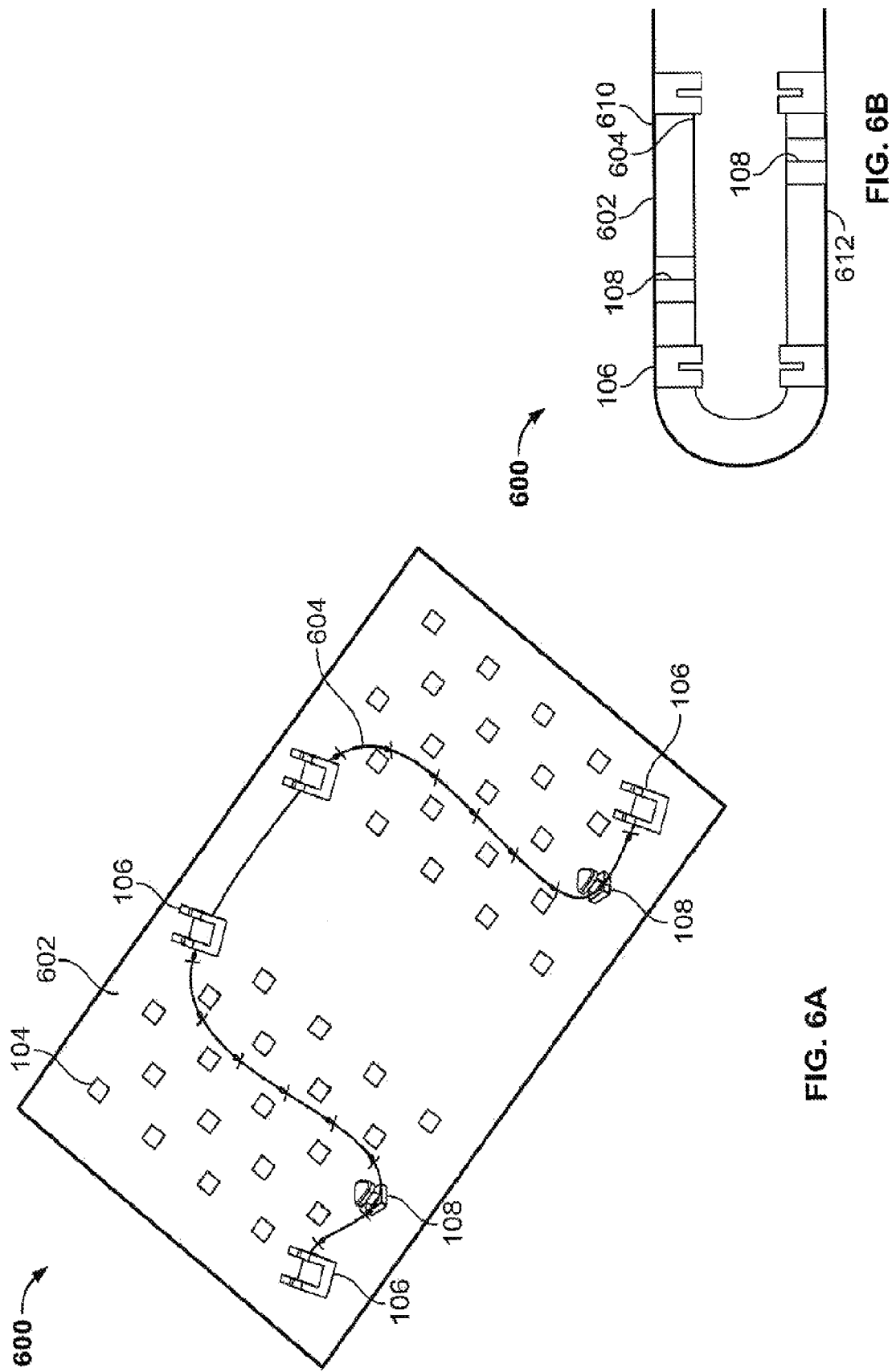

SUTURE PACKAGING AND METHODS RELATED THERETO

CROSS-REFERENCE TO RELATED APPLICATIONS

This application is the U.S. National Phase under 35 U.S.C. §371 of International Application No. PCT/US2008/075849, filed Sep. 10, 2008, which claims priority to U.S. Provisional Patent Application No. 60/971,135, filed Sep. 10, 2007. The corresponding International Application was published on Mar. 19, 2009. The above-referenced applications are hereby incorporated by reference in their entireties.

FIELD OF THE INVENTION

The present invention relates generally to packaging for sutures and methods related thereto.

BACKGROUND

Sutures typically consist of a filamentous suture thread attached to a needle with a sharp point. Sutures may be conventional or self-retaining. Self-retaining sutures (often referred to as "barbed sutures") differ from conventional sutures in that they possess numerous tiny retainers (often barbs) which anchor into the surrounding tissue following deployment, thereby eliminating the need to tie knots to affix adjacent tissues together. A self-retaining suture may be uni-directional, having one or more retainers oriented in one direction along the length of the suture thread; or bidirectional, typically having one or more retainers oriented in one direction along a portion of the thread, followed by one or more retainers oriented in another (often opposite) direction over the remainder of the thread. Although any number of sequential or intermittent configurations of self-retaining sutures are possible, the most common form involves a needle at one end, followed by barbs projecting from the suture thread and "away" from the needle until the transition point (often the midpoint) of the suture is reached; at the transition point the configuration of barbs reverses itself 180° (i.e., the barbs are now facing in the opposite direction) along the remaining length of the suture thread before the suture thread is attached to a second needle at the opposite end.

Various types of packaging for sutures have been used and currently exist in commercial form today. Most suture package designs feature a housing wherein the suture material is bunched together, coiled together, or wound into an oval or "figure 8" configuration. These suture package designs typically allow the suture material to contact itself and/or the suture packaging in multiple areas. Such designs are suboptimal for several reasons. Suture material tends to have a "memory" whereby the suture material retains the shape it had while it was stored, even after deployment. Accordingly, suture material that is bunched, coiled together or wound into a oval or "figure 8" configuration during storage may revert back to its storage configuration and thus may have a tendency to grab or become entangled with itself when used in the operating field. Coiling or winding of barbed sutures within the packaging can be an issue with barbed sutures, because the barbs may flatten during storage and retain that flattened shape when deployed, thereby decreasing the effectiveness of the barbs in the operating field. Most suture packages are also designed to have only a single configuration (i.e., they are unalterable). Consequently, these suture packages often lack the flexibility to effectively store different types of sutures in different configurations based on the specific properties of the suture being stored therein. To overcome various issues in this art, such as those mentioned above, as well as other issues in the art, it would be desirable to provide an improved suture package which can be altered based on the properties of the suture being stored, configured to minimize issues associated with suture memory, and configured to minimize points at which the packaged suture intersects with itself and the suture package during storage.

BRIEF SUMMARY OF THE INVENTION

Briefly stated, the present invention provides suture packages, and methods for making the same, for the retention, deployment and sale of sutures. Within one aspect of the present invention suture packages are provided, comprising (a) a panel with a multiplicity of apertures, (b) at least one needle park selectively inserted into the apertures and adapted to secure a suture to the suture package; and (c) at least one wrapping peg selectively inserted into the apertures and adapted to guide the suture within the suture package. Within one embodiment, the panel may optionally comprise a first panel surface and a second panel surface, with the first panel surface joined to the second panel surface with a hinge; and each panel surface may include a multiplicity of apertures and at least one of the needle parks selectively inserted into one of the apertures of the first panel surface and into one of the apertures of the second panel surface; and at least one of the wrapping pegs selectively inserted into one of the apertures of the first panel surface and into one of the apertures of the second panel surface; and wherein the first panel surface can be folded over in order to face the second panel surface.

Within another aspect of the present invention, a needle park is provided which is adapted to retain a suture and to be selectively inserted into a suture package panel, comprising: (a) a suture park body having a top end and a bottom end; (b) a needle park slot on the top end of the suture park body; (c) a channel located at an angle to the needle slot; and (d) a mounting lug attached to the bottom end of the suture park body.

Within various aspects of the present invention, suture packages are provided which can be used, or which are adapted for use in endoscopic surgery.

Within yet other aspects of the present invention, methods for applying a suture to a patent including the steps of: (a) removing a first needle from a first needle park of a package by placing an instrument into a channel of the first needle park and around the first needle and urging the first needle out of a retaining slot of the first needle park; (b) removing at least part of a suture thread connected to the first needle; (c) applying the first needle and at least part of the suture thread to a patient; (d) removing a second needle from a second needle park of the package by placing the instrument into a channel of the second needle park and around the second needle and urging the second needle out of a retaining slot of the second needle park; and (e) applying the second needle and at least part the suture thread to a patient.

The details of one or more embodiments are set forth in the description below. Other features, objects and advantages will be apparent from the description, the drawings, and the claims. In addition, the disclosures of all patents and patent application referenced herein are incorporated by reference in their entirety.

BRIEF DESCRIPTION OF THE DRAWINGS

The accompanying drawings, which are incorporated into and constitute a part of this specification, illustrate one or more embodiments and, together with the detailed description, serve to explain the principles and implementations of the invention. In the drawings:

FIG. 4A illustrates a top perspective view of an embodiment of a wrapping peg.

FIG. 4B illustrates a top cross-sectional view of the wrapping peg illustrated in FIG. 4A.

FIG. 6A illustrates a top view of an embodiment of the suture package.

FIG. 6B illustrates a side view of the embodiment of the suture package illustrated in FIG. 6A.

DETAILED DESCRIPTION

Figure 1:
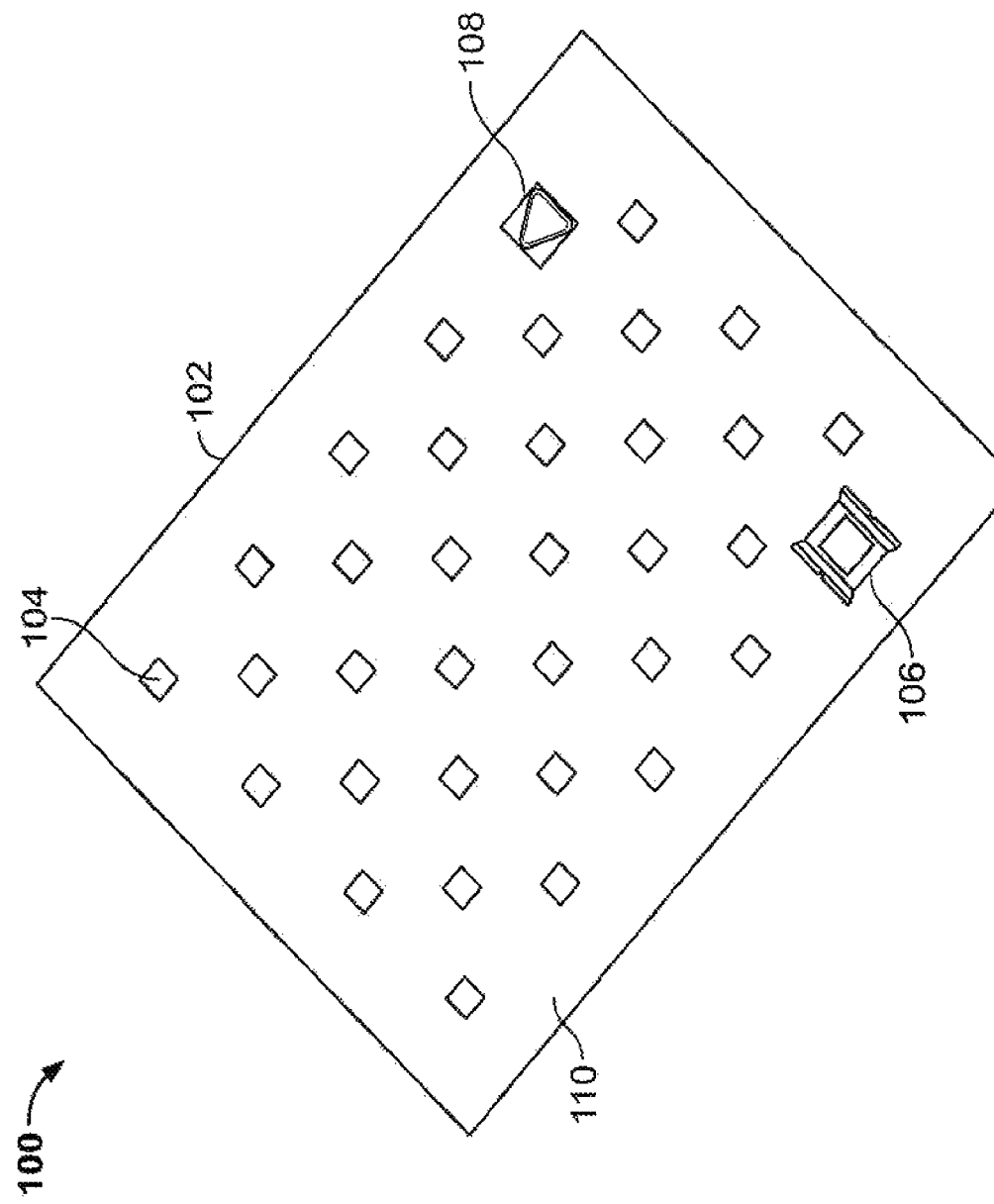
FIG. 1 illustrates top perspective view of an embodiment of the suture package, according to the present invention.

Prior to setting forth detailed embodiments of the invention, it may be helpful to an understanding thereof, to first set forth definitions of certain terms that are used hereinafter.

"Suture package" (or "package" or "dispenser") refers to a device that can releasably hold at least one suture.

"Self-retaining system" refers to a self-retaining suture together with devices far deploying the suture into tissue. Such deployment devices include, without limitation, suture needles and other deployment devices as well as sufficiently rigid and sharp ends on the suture itself to penetrate tissue.

"Self-retaining suture" (or "barbed suture") refers to a suture that does not require a knot or a suture anchor at its end in order to maintain its position into which it is deployed during a surgical procedure. These may be monofilament sutures or braided sutures, and are positioned in tissue in two stages, namely deployment and affixation, and include at least one tissue retainer.

"Tissue retainer" (or simply "retainer" or "barb") refers to a suture element having a retainer body projecting from the suture body and a retainer end adapted to penetrate tissue. Each retainer is adapted to resist movement of the suture in a direction other than the direction in which the suture is deployed into the tissue by the surgeon, by being oriented to substantially face the deployment direction. As the tissue-penetrating end of each retainer, moving through tissue during deployment, faces away from the deployment direction (the direction of the passage of the suture during deployment), the tissue retainers should not catch or grab tissue during this phase. Once the self-retaining suture has been deployed, a force exerted in another direction, often substantially opposite to the deployment direction, to affix the suture in position, causes retainers to be displaced from their deployment positions (of resting substantially along the suture body) and causes retainer ends to penetrate into the tissue, resulting in tissue being caught between the retainer and the suture body. The retainers may all be deployed in one direction or they may be deployed in one direction at one end and in the other direction at the other end.

"Suture thread" refers to the filament component of the suture, and, for sutures requiring needle deployment, does not include the needle.

"Suture deployment end" refers to an end of the suture to be deployed into tissue; one or both ends of the suture may be suture deployment ends. The suture deployment end may be attached to deployment devices such as suture needles, or may be sufficiently sharp and rigid to penetrate tissue on its own.

"Armed suture" refers to a suture having a suture needle on at least one suture deployment end.

"Bidirectional suture" refers to a self-retaining suture having retainers oriented in one direction at one end and retainers oriented in the other direction at the other end. A bidirectional suture is typically armed at each end of the suture thread.

"Transition segment" refers to a retainer-free portion of a bidirectional suture located between a first set of retainers oriented in one direction and a second set of retainers oriented in another direction.

"Suture needle" (or simply "needle") refers to a needle used to deploy sutures into tissue, which come in many different shapes, forms and compositions. There are two main types of needles, traumatic needles and atraumatic needles. Traumatic needles have holes or eyes which are supplied separate from the suture thread and are threaded on site. Atraumatic needles are eyeless and are attached to the suture at the factory by swaging whereby the suture material is deformed to a final shape to hold the suture and needle together. Most modern sutures are swaged atraumatic needles. Suture needles are described, for example, in U.S. Pat. Nos. 6,322,581 and 6,214,030 (Mani, Inc., Japan); and 5,464,422 (W.L. Gore, Newark, Del.); and 5,941,899; 5,425, 746; 5,306,288 and 5,156,615 (US Surgical Corp., Norwalk, Conn.); and 5,312,422 (Linvatec Corp., Largo, Fla.); and 7,063,716 (Tyco Healthcare, North Haven, Conn.). Other suturing needles are described, for example, in U.S. Pat. Nos. 6,129,741; 5,897,572; 5,676,675; and 5,693,072. All of these patents are incorporated herein by reference.

"Needle park" refers to a holder on which a needle or suture thread is secured in the suture package.

"Suture peg" (or simply "peg") refers to an upright support which can support and guide a suture thread in a package.

Embodiments are described herein in the context of a suture packaging and methods related thereto. Those of ordinary skill in the art will realize that the following detailed description is illustrative only and is not intended to be in any way limiting. Other embodiments of the present invention will readily suggest themselves to such skilled persons having the benefit of this disclosure. Reference will now be made in detail to implementations of embodiment of the present invention as illustrated in the accompanying drawings. The same reference indicators will be used throughout the drawings and the following detailed description to refer to the same or like parts.

FIG. 1 illustrates an embodiment of a suture package. The suture package, generally numbered 100, includes a panel 102 with apertures 104, a needle park 106 inserted into an aperture and a wrapping peg 108 inserted into an aperture. The panel 102 is illustrated as being square shaped and having a single surface for receiving needle parks 106 and wrapping pegs 108; however, it is contemplated that the panel 102 may have a variety of different configurations as will be hereinafter described in greater detail. The panel 102 can be made of cardboard, plastic or any other material as envisioned by one with ordinary skill in the art without deviating from the scope of this invention. The panel 102 includes a multiplicity of apertures 104 which in this embodiment are evenly distributed in a plurality of aligned vertical columns and horizontal rows throughout the top surface 110 of the panel 102. Nevertheless, despite being illustrated as having regular patterns and being evenly distributed, it is envisioned that the apertures 104 can be arranged in any pattern and have any shape without deviating from the scope of this invention. While the apertures 104 may have any shape, it is preferable that the apertures have a restricted configuration. An aperture has a restricted configuration to prevent twisting and turning of the needle parks 106 and wrapping pegs 108 inserted into the apertures and to allow for specific orientation of the needle parks 106 and wrapping pegs 108 within the panel 102. The apertures 104 illustrated in FIG. 1 are square-shaped (or cube-shaped in three dimensions) which would constitute a restricted configuration. Other aperture 104 shapes such as triangles, pentagons, octagons, etc., would also be considered apertures having a restricted configuration. Needle parks 106 can be used to releasably secure a suture needle and/or a suture thread to the panel 102. Wrapping pegs 108 can be used to support and/or guide a suture thread on the panel 102. Needle parks 106 and wrapping pegs 108 will be described in greater detail below. The needle parks 106 and the pegs 108 can be removably and selectively inserted into any aperture 104 in the panel 102. Accordingly, the suture package 100 is selectively adaptable to facilitate multiple needle park 106 and peg 108 configurations to yield the best winding configuration for the suture stored therein based on the specific properties of the suture.

Figure 2:
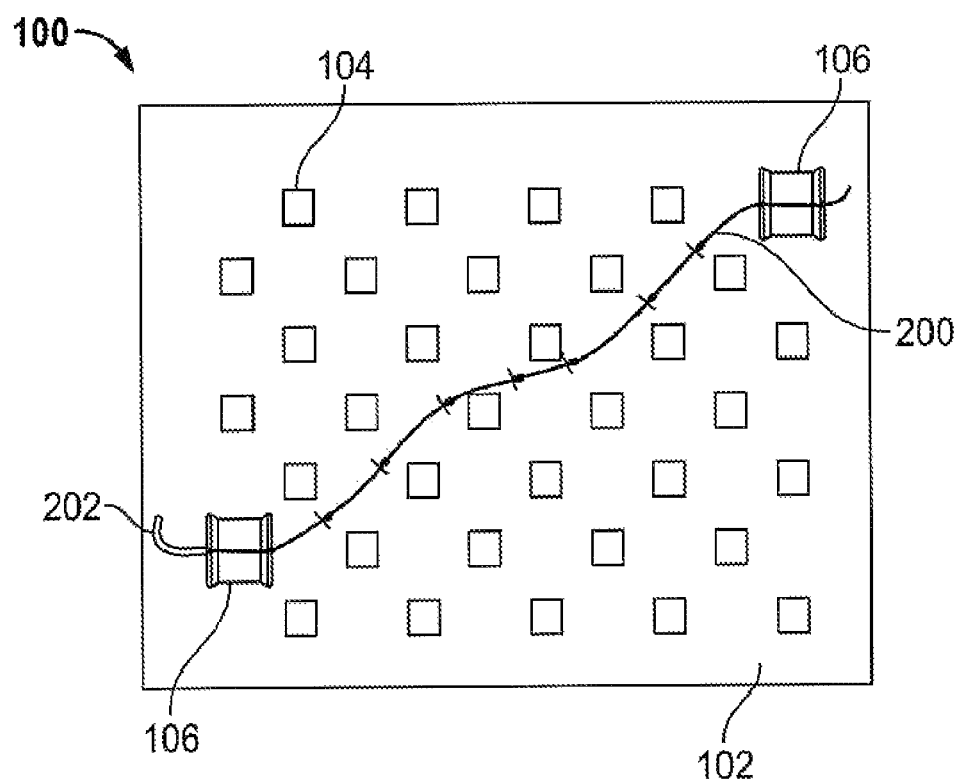
FIG. 2 illustrates a top plan view of an embodiment of the suture package.

FIG. 2 illustrates an embodiment of the suture package 100. FIG. 2 illustrates a panel 102, apertures 104, needle parks 106, and a barbed suture thread 200 including a needle 202 connected to the barbed suture thread 200 (collectively a single armed suture). In this configuration, two needle parks 106 are removably inserted into the panel 102 at opposite ends. The needle 202 is attached to a needle park 106, while the other end of the suture thread 200 is attached to another needle park 106. The suture thread 200 is maintained in a straight configuration in this embodiment, thereby eliminating the likelihood of the suture retaining any "memory" of a coiled or otherwise bent configuration in the suture package 100.

Figure 3:
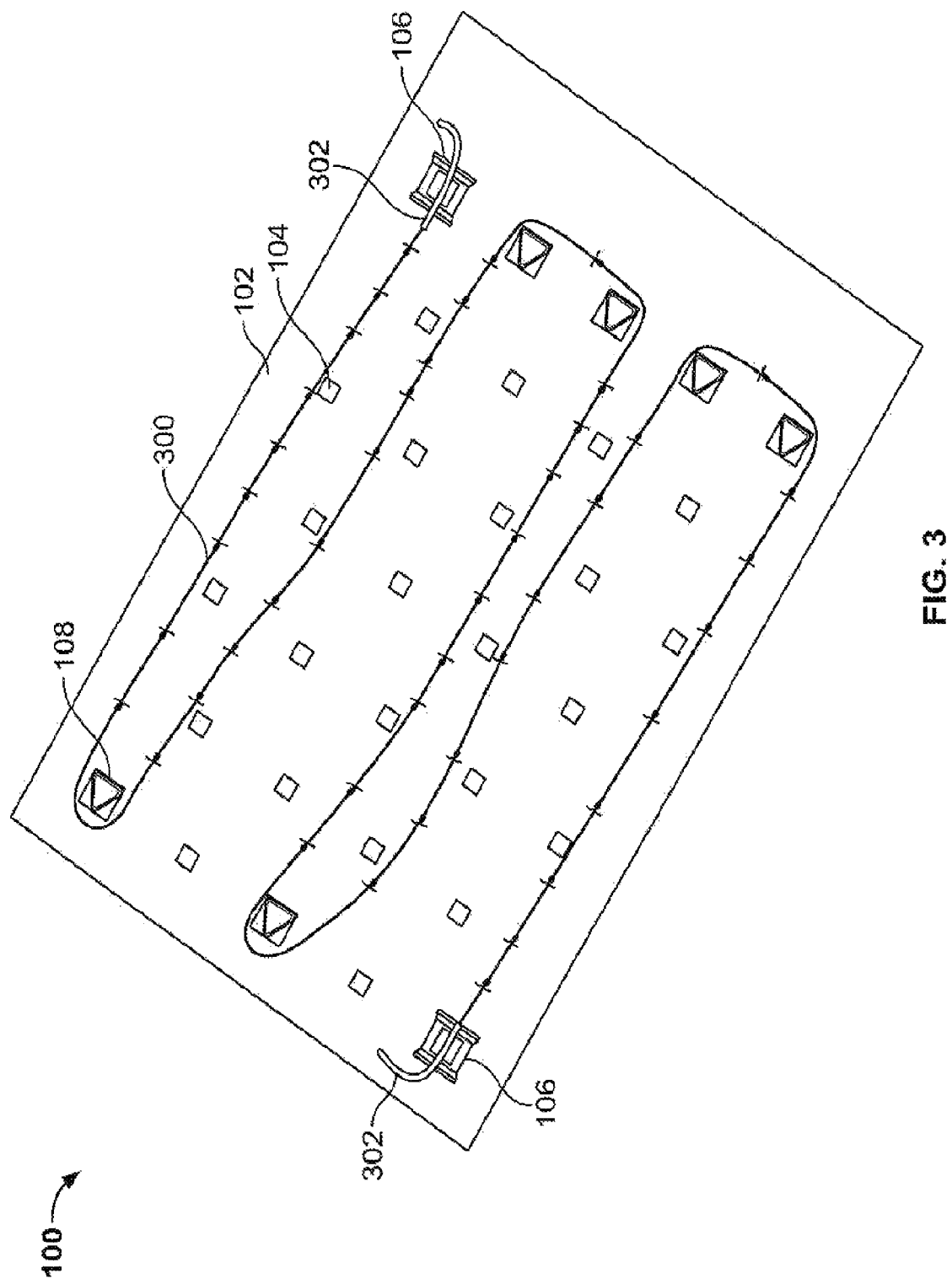
FIG. 3 illustrates a top plan view of an embodiment of the suture package.

FIG. 3 illustrates an embodiment of the suture package 100. FIG. 3 illustrates a panel 102, apertures 104, needle parks 106, wrapping pegs 108, a barbed suture thread 300, and needles 302 connected to the barbed suture thread 300. Similar to the configuration illustrated in FIG. 2, two needle parks 106 are removably inserted into the panel 102 at opposite ends, in this embodiment, the needles 302 are releasably attached to the needle parks 106. The suture thread 300 is wrapped around the wrapping pegs 108 in a serpentine configuration. In this configuration, a longer suture thread 300 can be stored within the suture package 100, wherein the suture thread does not contact itself and contact between the suture thread 300 and the suture package 100 is minimized. It is understood that any combination of needle parks 106 and wrapping pegs 108 can be used within the suture package 100 depending on the specific properties of the suture being stored or based on a configuration requested by the end user.

FIG. 4A illustrates an embodiment of a wrapping peg 400. The wrapping peg 400 in this embodiment includes a post 402 having a first end 404 and a second end 406, a retaining cap 408, a retaining base 410 having a first side 412 and a second side 414, and a peg mounting lug 416. The retaining cap 408 is attached to the first end 404 of the post 402. The second end 406 of the post 402 is attached to the first side 412 of the retaining base 410. The peg mounting lug 416 is attached to the second side 414 of the retaining base 410. The peg mounting lug 416 can be inserted into an aperture 104 in the panel 102 (shown in FIG. 1), thereby securing the wrapping peg 400 to the suture package 100. A peg mounting lug 416 has a restricted configuration to prevent twisting or turning of the wrapping peg 400 when inserted into an aperture, and to allow for specific orientation of the wrapping peg 400 within the panel 102. The peg mounting lug 416 illustrated in FIG. 4A is square-shaped which would constitute a restricted configuration. The square-shaped mounting lug 416 preferably snugly fits into a square-shaped aperture 104. Other peg mounting lugs shaped as triangles, pentagons, octagons, etc., would also be considered peg mounting lugs having a restricted configuration. It is envisioned that the wrapping peg 400 can be any plastic, rubber or polymer made from any inert material such as, but not limited to, silicone. A suture thread can be wound, spooled, guided, supported or otherwise organized within a suture package using a wrapping peg 400.

The retaining cap 408 and the retaining base 410 can be used as boundaries to keep the suture thread in place on the post 402 within the suture package. The retaining cap 408 is illustrated as having a generally triangular shape, and the retaining base 410 is illustrated as having a generally square shape. Nevertheless, it is envisioned that the retaining cap 408 and the retaining base 410 may have any shape. In an embodiment, the wrapping peg may not have a peg mounting lug 412, wherein the retaining base 410 is inserted directly into an aperture. The peg may also not have a retaining cap 408 and/or a retaining base 410. Thus, the post 402 may constitute the entire wrapping peg.

Referring to FIG. 4B, it can be seen that the post 402 includes rounded corners having a small radius 418. This allows the post 402 to minimally affect the suture thread wrapped around the post 402, by minimizing the contact area between the post 402 and the suture thread. This is especially beneficial with respect to barbed suture threads. A barbed suture thread wrapped around a round post may cause many individual barbs to be flattened against the post, whereas a post 402 including rounded corners having a small radius 418 may only affect a small number of individual barbs, if any at all. In an embodiment, the post 402 can be selectively positioned to place the rounded corner having a small radius 418 between individual barbs to avoid pressing down on any barbs. Generally a triangular shaped post 402 will provide the most advantageous shape for the post 402 to minimize contact with the suture. While the post 402 is illustrated as having a triangular shape, it is envisioned that the post 402 can have any shape which includes rounded corners having a small radius (e.g., square, pentagon, etc.).

It is noted that wrapping pegs may also generally include without limitation: spools (stationary or rotatable), reels and winding elements around which a suture may be wound, arches or bridges under which the suture may pass in a coil, eccentric guide elements around which a suture can be wound (such that the guide elements act something like a foci in an ellipse), and so forth without deviating from the scope of this invention. The panel can also include one or more perforations through which a suture may pass (thus using the panel itself as a guide element).

Figure 5:
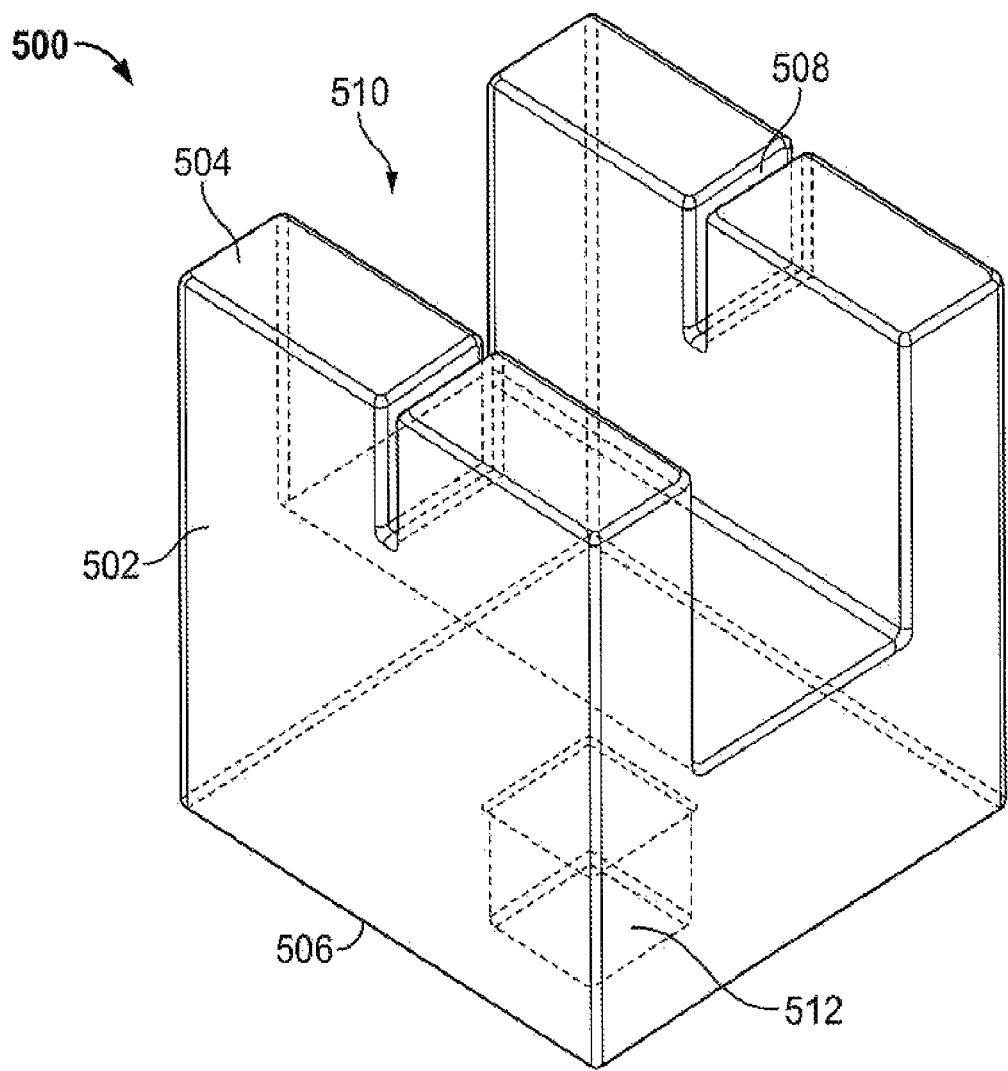
FIG. 5 illustrates a top perspective view of an embodiment of a needle park.

FIG. 5 illustrates an embodiment of a needle park 500. The needle park 500 in this embodiment includes a needle park body 502 having a top end 504 and a bottom end 506, a needle park slot 508, a needle park channel 510, and a needle park mounting lug 512. The needle park slot 508, which is located on the top end 504 of the needle park body 502, can be used to secure a suture needle 312 and/or a suture thread 310 (as shown in FIG. 3). The needle park channel 510, also located on the top end 504 of the needle park body 502 can be situated perpendicular to the needle park slot 508. In an embodiment, the depth of the needle park channel 510 into the needle park body 502 is greater than the depth of the needle park slot 508 into the needle park body 502. The needle park channel 510 is also wider than the width of the needle park slot 508. In an embodiment, the needle park channel 510 is at least wide enough to allow needle holders/drivers to grasp the needle or suture thread to remove it from the needle park 500. The needle park mounting lug 512 can be removably and selectively inserted into an aperture 104 in the panel 102 (shown in FIG. 3), thereby securing the needle park 500 to the suture package 100 in the desired position on the panel 102. A needle park mounting lug 512 has a restricted configuration to prevent twisting or turning of the needle park 500 when inserted into an aperture and to allow for specific orientation of the needle park 500 within the panel 102. The needle park mounting lug illustrated in FIG. 5 is square-shaped which would constitute a restricted configuration. The square-shaped needle park mounting lug 512 preferably snugly fits into a square-shaped aperture 104. As with the wrapping peg mounting lug 416, other needle park mounting lugs shaped as triangles, pentagons, octagons, etc., would also be considered needle park mounting lugs having a restricted configuration. In an embodiment, the needle park may not have a needle park mounting lug 512, wherein the needle park body 502 is directly inserted into an aperture. It is envisioned that the needle park 500 can be any plastic, rubber or polymer made from any inert material such as, but not limited to, silicone.

It is noted that needle parks may also generally include without limitation: spools (stationary or rotatable), reels and winding elements around which a suture may be wound, arches or bridges under which the suture may pass in a coil, eccentric guide elements around which a suture can be wound (such that the guide elements act something like a foci in an ellipse) and so forth without deviating from the scope of this invention. The panel can have one or more perforations in the panel of a suture package wherein a needle can be secured to the panel (thus using the panel itself as a needle park).

As set forth above, the suture packaging panel can have a variety of configurations. FIG. 6A provides an illustration of an embodiment of the suture package. FIG. 6A illustrates a foldable panel 602 having apertures 104, needle parks 106, wrapping pegs 108, and a suture 604. The needle parks 106 and the wrapping pegs 108 are removably inserted into the apertures 104. Alternatively the needle parks 106 and the wrapping pegs 108 may be fixedly inserted into the apertures 104. The suture package 600 can have an open and a closed configuration. In the open configuration, a suture 604 can be secured to the suture package 600 using any combination of needle parks 106 and wrapping pegs 108. The panel 602 can then be folded to a closed configuration as illustrated in FIG. 6B. This embodiment may increase the total area of the packaging panel while decreasing the space needed to store the suture package. This embodiment may also help protect the suture 604 during storage. In an embodiment, the needle parks 106 and wrapping pegs 108 can be on opposite sides of each other to space the opposite sides of the folded panel 602 apart. For example, opposing needle parks 106 and wrapping pegs 108 can touch each other or can touch opposing portions of the panel to keep the opposing sides (such as sides 610 and 612) of the panel apart.

Figure 7A:
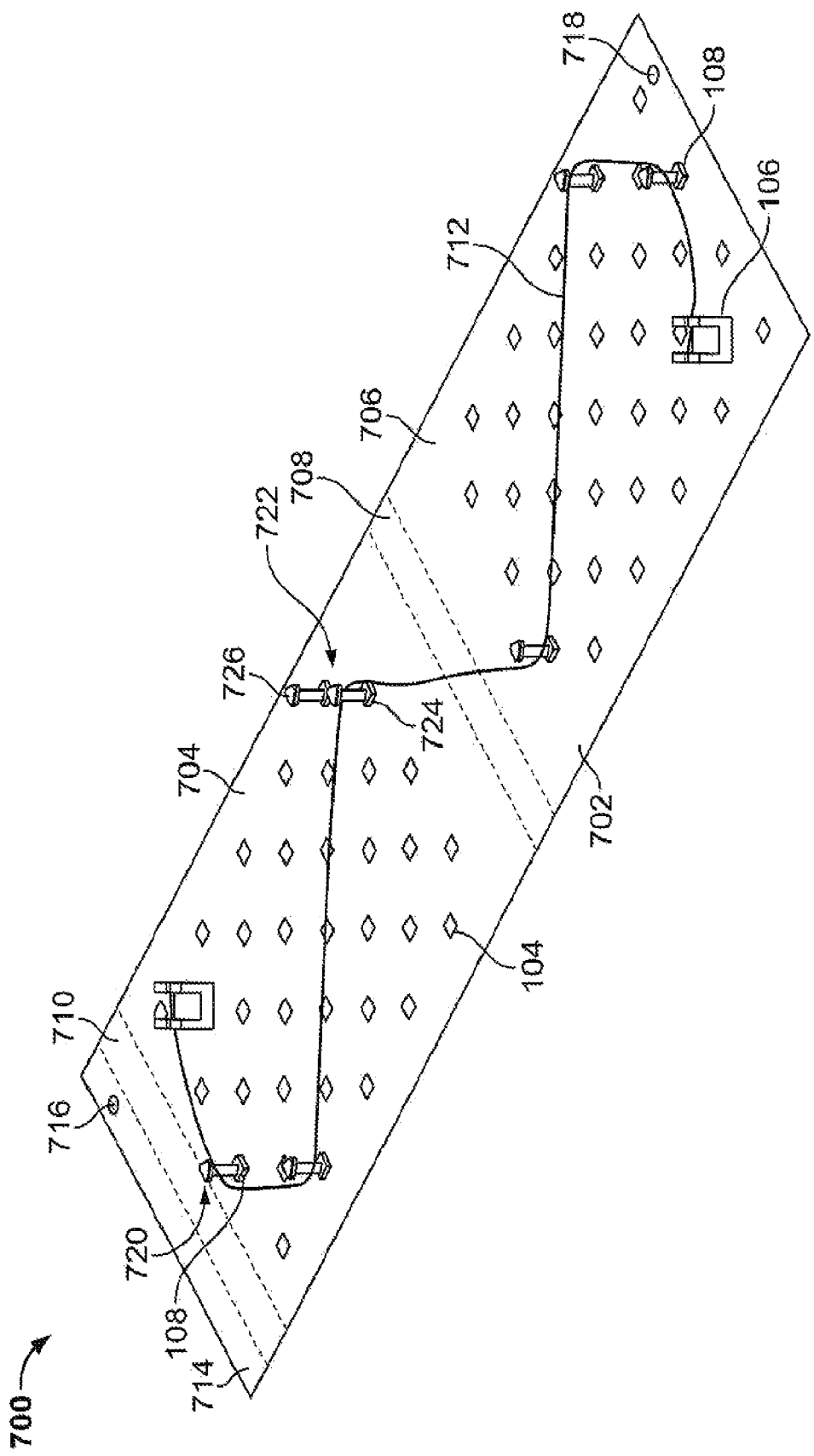
FIG. 7A illustrates a top perspective view of an embodiment of the suture package.

FIG. 7A illustrates an embodiment of the suture package. The suture package, generally numbered 700, includes a foldable panel 702 having a first surface 704 and a second surface 706, a first side edge 708 and a second side edge 710, apertures 104, needle parks 106, pegs 108, an end flap 714, a lock tab 716 and a lock tab slot 718. The first side edge 708 hingedly connects the first surface 704 to the second surface 706. The second side edge 710 hingedly connects the first surface 704 to the end flap 714. The needle parks 106 and the wrapping pegs 108 are removably inserted into the apertures 104. The suture package 700 can have an open and a closed configuration. A suture 712 can be secured to the needle parks 106 and pegs 108 while the suture package 700 is in its open configuration. Once the suture is secured to the suture package 700, the second surface 706 can be folded over the first surface 704 along the first side edge 708. The end flap 714 can then be folded and secured to the back of the second surface 706 by mating the lock tab 716 to the lock tab slot 718. Of course, it is to be understood that the tab/slot combination is only one of many fastening means that would be obvious to one skilled in the art. The suture package 700 thus forms a rectangular box in its closed configuration. The suture package 700 is also adaptable and capable of multiple needle park 106 and wrapping peg 108 configurations depending on the specific properties of the suture being stored or based on a configuration requested by the end user. FIG. 7A depicts winding pegs in an unrestricted configuration 720 and in a restricted configuration 722. In the unrestricted configuration 720, only one peg 108 is preferably used with the suture 712 wound around only a portion of the peg 108. In a restricted configuration 722, two or more pegs 108 are used to confine or restrict the suture. As depicted the restricted configuration 722 includes a first peg 724 around which the suture is partially wound with a second peg 726 placed adjacent the first peg and with the suture between the first and second pegs. The first and second pegs 724, 725 thus act as a restrictive gate limiting the potential movement relative to either of the first and second pegs individually.

Figure 7B:
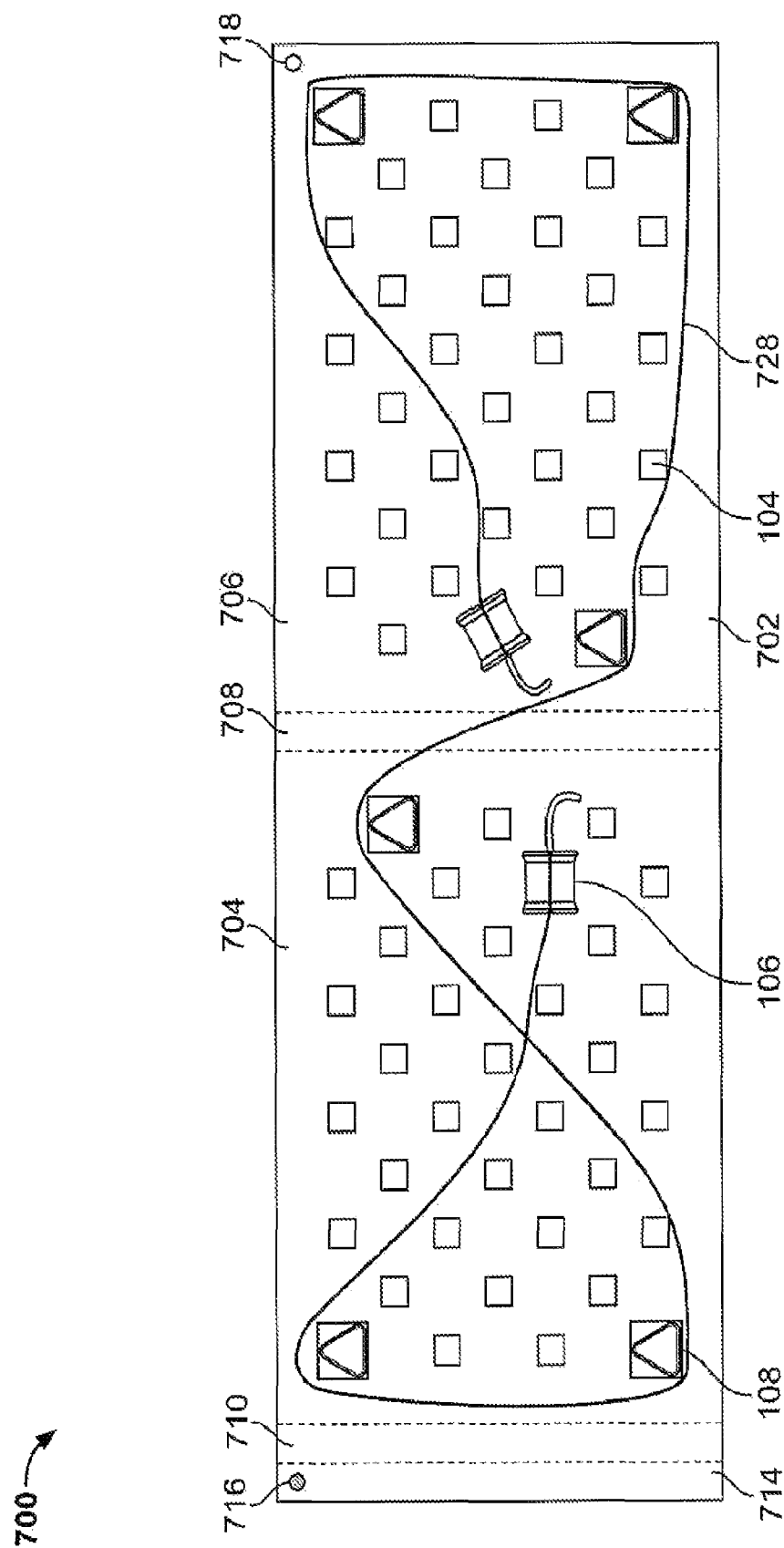
FIG. 7B illustrates a top plan view of an embodiment of the suture package.
Figure 7C:
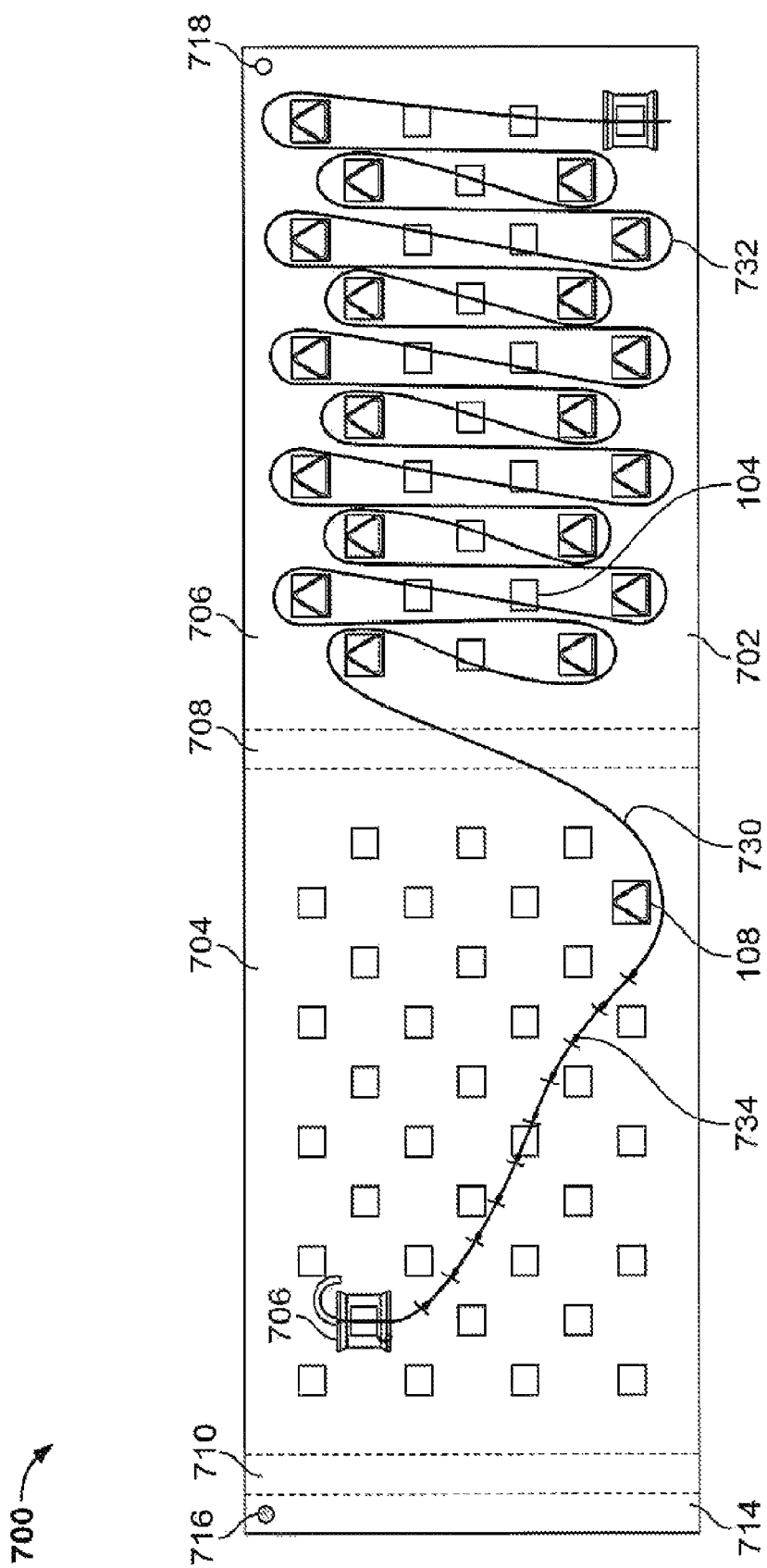
FIG. 7C illustrates a top plan view of an embodiment of the suture package.
Figure 7D:
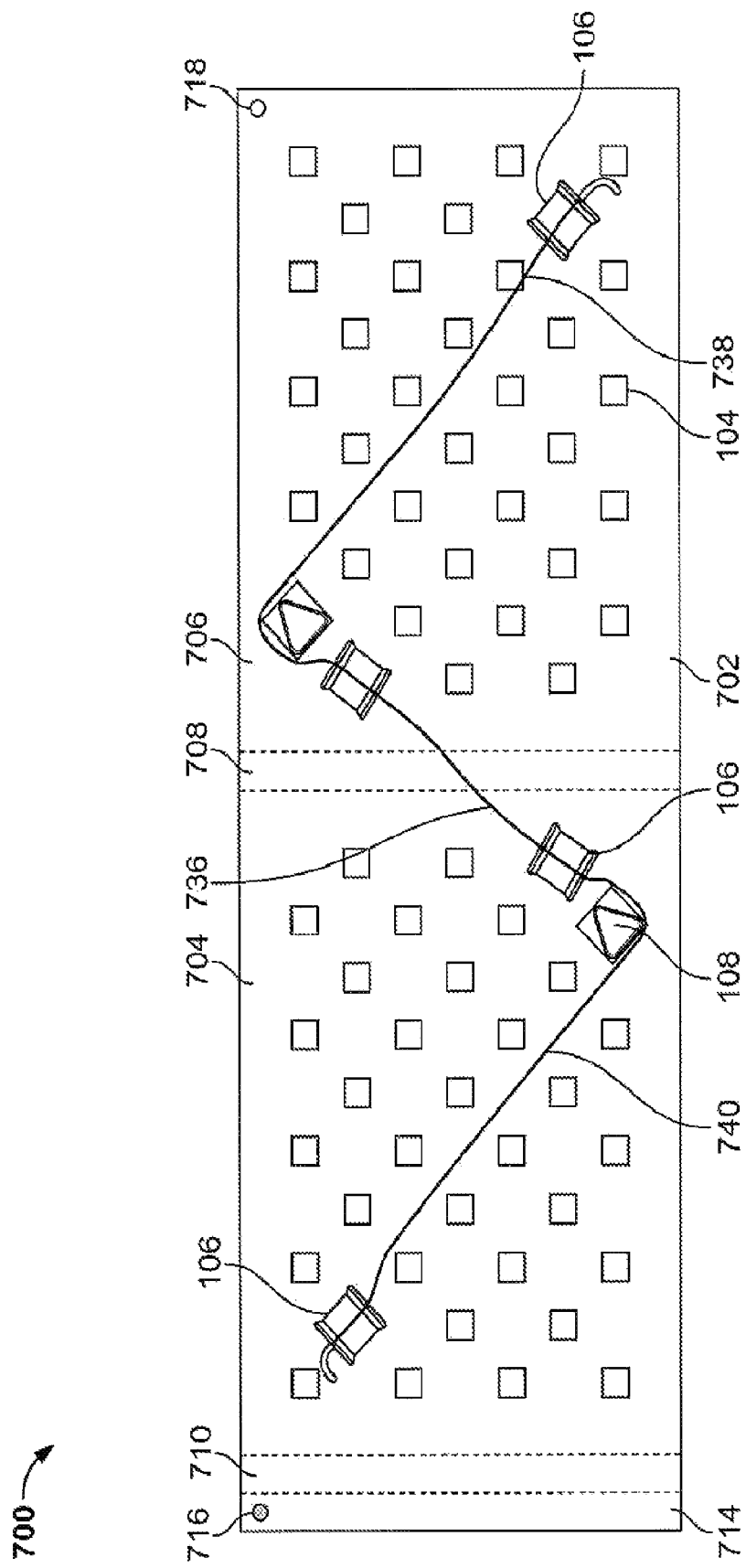
FIG. 7D illustrates a top plan view of an embodiment of the suture package.

Examples of these different needle park 106 and wrapping peg 108 configurations are illustrated in FIGS. 7B, 7C and 7D. FIG. 7B depicts a double armed (two needles) suture 728 that is fully deployed on the panel 702. FIG. 7C depicts an asymmetrically barbed suture 730 that is deployed on the panel 702. In this embodiment, the unbarbed portion of the suture 732 is closely wound around the pegs 108 in a serpentine pattern on one of the surfaces of the panel 706 and the barbed portion of the suture 734 is held between one peg 108 and the needle park 106 on the other surface of the panel 704 so that the barbs are not compressed down on the suture by any peg 108 or needle park 106. FIG. 7O depicts a double armed suture 736 wherein the suture 736 is secured to the panel 702 by two needle parks 106 on both sides 704, 706 of the panel 702. In this embodiment and during a surgical or cosmetic procedure, a first portion of the suture 738 can be deployed from the suture package 700 while a second portion of the suture 740 remains secured to the package 700. The suture 736 can thus be deployed in stages to prevent the suture 736 from becoming tangled during use.

Figure 8:
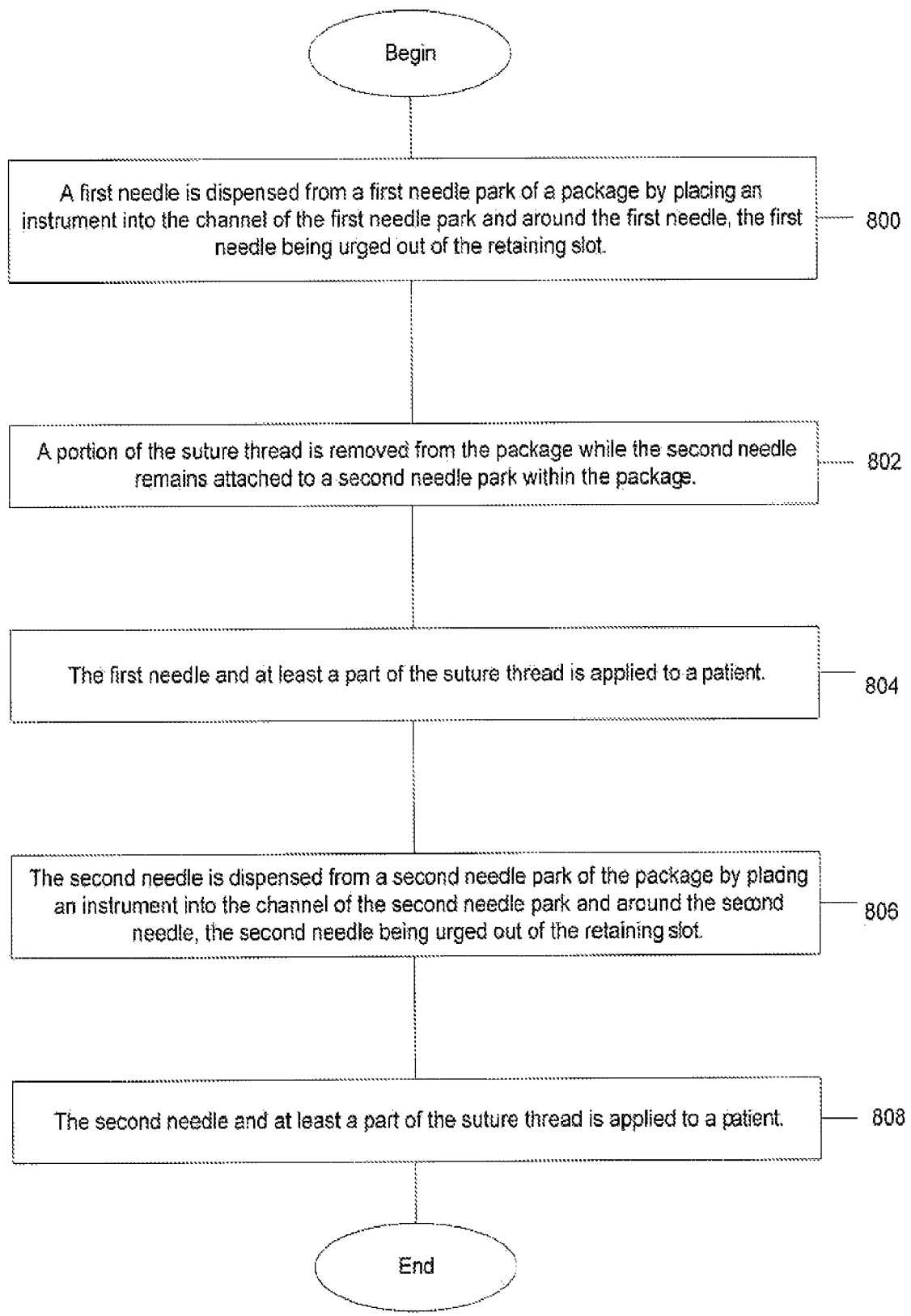
FIG. 8 is a flow chart showing a method of dosing a wound using an embodiment of the invention.

FIG. 8 illustrates a method of the invention for applying a double-armed suture (barbed or conventional) to a patient in accordance with some embodiments of the present invention, the structural embodiment of the suture package having been discussed above. As illustrated in FIG. 8, a first needle is dispensed from a first needle park of a package by placing an instrument into the channel of the first needle park and around the first needle. The first needle is then urged out of the retaining slot (800). A portion of the suture thread is removed from the package while the second needle remains attached to a second needle park within the package (802). The first needle and at least a part of the suture thread is applied to a patient (804). The second needle is dispensed from a second needle park of the package by placing an instrument into the channel of the second needle park and around the second needle. The second needle is then urged out of the retaining slot (806). The second needle and at least a part of the suture thread is applied to a patient (808).

Figure 9:
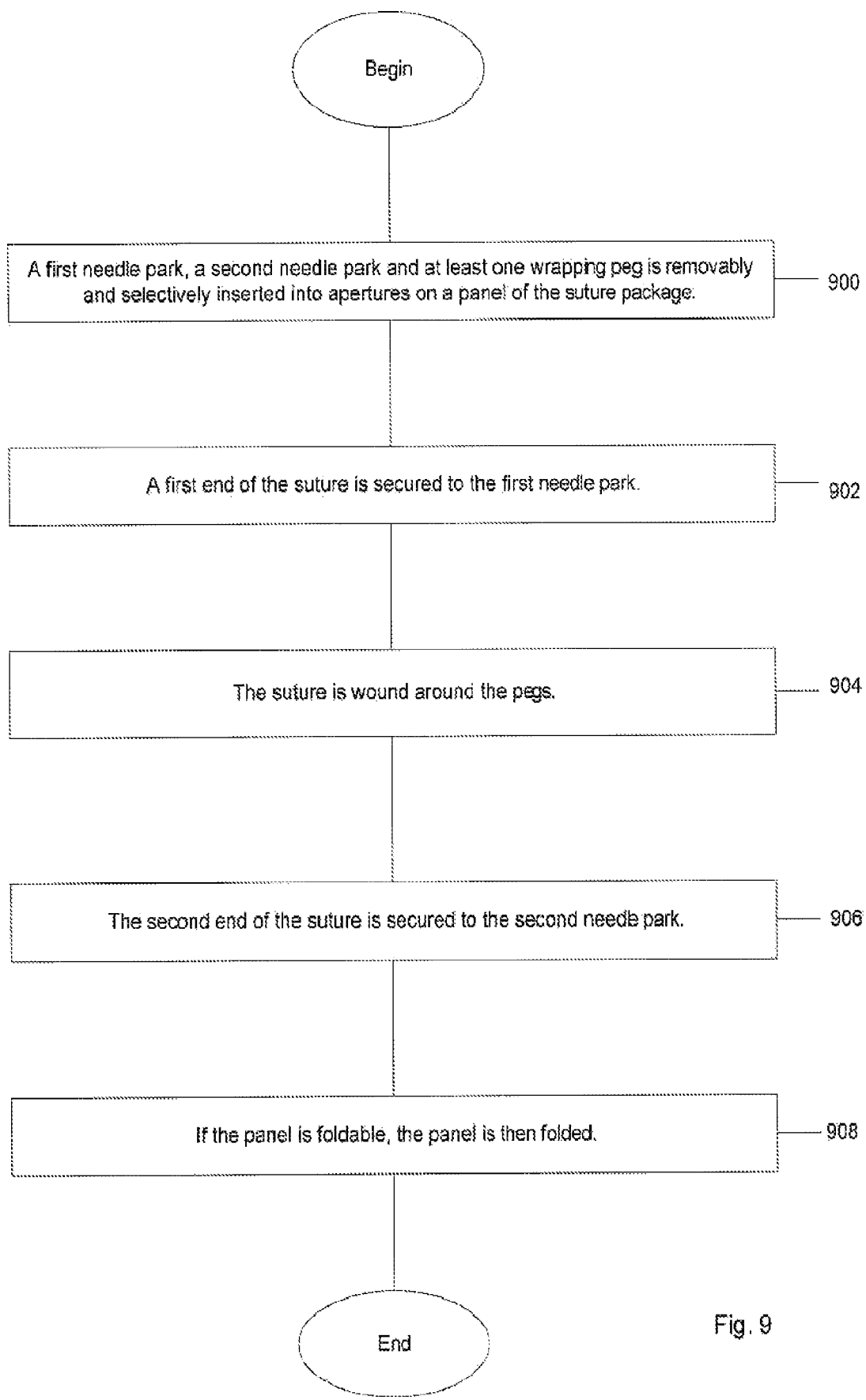
FIG. 9 is a flow chart showing a method for automated packaging of sutures in an embodiment of the invention.

FIG. 9 illustrates a method of the invention for automated packaging of sutures in a suture package. As illustrated in FIG. 9, a first needle park, a second needle park and at least one wrapping peg is removably or fixedly and selectively inserted into apertures on a panel of the suture package (900). A first end of the suture is secured to the first needle park (902). The suture is then wound around the pegs (904). The second end of the suture is then secured to the second needle park (904). Alternatively, if needles are attached to the end of the suture, the needles are retained in the needle parks. If the panel is foldable, the panel is then folded (906).

It is worth noting that these suture packages may be manufactured from any suitable materials and may have sutures packaged into them during the manufacturing process or after the packages are manufactured. Some of these examples describe suture packages in which sutures are fully sealed and therefore can be maintained in sterility, but it is to be understood that any of the packages disclosed herein can be further enclosed in sealed containers which would facilitate maintaining sterility. Furthermore, these suture packages or sutures may be provided with compositions to facilitate dispensing of the sutures, to inhibit growth of bacteria, fungi, or other contaminants, or to be transferred on to the sutures themselves (such as compounds to promote healing and prevent undesirable effects such as scar formation, infection, pain, and so forth). This can be accomplished in a variety of manners, including for example: (a) by directly affixing to the desired surface(s) of the package or suture a formulation (e.g., by either spraying the suture with a polymer/drug film, or by dipping the suture into a polymer/drug solution), (b) by coating the desired surface(s) of package or suture with a substance such as a hydrogel which will in turn absorb the composition, or (c) manufacturing the package or suture itself with a composition. Such compositions may include without limitation anti-proliferative agents, anti-angiogenic agents, anti-infective agents, fibrosis-inducing (or "pro-healing") agents, anti-scarring (or anti-adhesion) agents, lubricious agents, echogenic agents, radio-opaque agents (and/or agents that enhance visualization under X-ray, CT, MRI and/or PET scanning), anti-inflammatory agents, cell cycle inhibitors, radioactive isotopes, analgesics, anaesthetics and anti-microtubule agents. For example, without limitation, the surfaces of a package that may contact the suture may have a composition applied thereto prior to the packaging of the suture, so that when the suture is dispensed from the package the composition may contact and adhere to the suture. Furthermore, any part of the package with which the suture comes into contact may be provided with the composition, such as surfaces of the base or, if a suture passes through the base, then the passage in the base. Alternatively, the suture package may include a composition-dispensing container through which the suture may be passed prior to deployment into tissue. It is noted that the aperture pattern on the suture packages described above facilitates even distribution of sterilization gases (e.g., EtO gas) for effective sterilization. The purpose of the suture may also determine the sort of composition that is applied to the suture package or suture; for example, anti-proliferative coatings (drugs or radioactive isotopes) may be desired for packages for sutures used in closing tumour excision sites, packages containing self-retaining sutures for use in tissue repositioning procedures may be provided with fibrosing (agents that promote wound healing) coatings, and those having anti-scarring or anti-infective coatings may be used for wound closure sutures. Coatings may also include a plurality of compositions either together or on different portions of the suture, where the multiple compositions can be selected for different purposes (such as combinations of analgesics, anti-infective and anti-scarring agents). The purpose of the suture may also determine the size of the suture package. For example, lower gauge sutures (such as those intended for orthopaedic surgery) may necessitate larger suture packages than those used for higher gauge sutures such as ophthalmic sutures. Similarly, suture packages for sutures intended for use in endoscopic surgery may be adapted for use with such endoscopic surgical equipment, for example, being configured suited to permit delivery of such a suture package to the surgical site (such as through an access port in the equipment).

While embodiments and applications of this invention have been shown and described, it would be apparent to those skilled in the art having the benefit of this disclosure, that many more modifications than mentioned above are possible without departing from the inventive concepts herein.

What is claimed is:

1. A suture package comprising:
   a panel with a multiplicity of apertures, said panel including a first panel surface and a second panel surface, with the first panel surface joined to said second panel surface with a hinge;
   at least one needle park selectively inserted into the apertures and adapted to secure a suture to the suture package; and
   at least one wrapping peg selectively inserted into the apertures and adapted to guide the suture within the suture package;
   wherein each panel surface includes a multiplicity of said apertures and said at least one needle park is selectively inserted into one of said apertures of said first panel surface and into one of said apertures of said second panel surface; and
   at least one of said wrapping pegs is selectively inserted into one of said apertures of said first panel surface and into one of said apertures of said second panel surface; and
   wherein said first panel surface can be folded over in order to face said second panel surface.

2. The suture package of claim 1 wherein said first panel includes a tab with a tab lock and said second panel surface includes a tab lock slot, and with said first panel surface facing said second panel surface said tab lock can be locked in said tab lock slot.

3. The suture package of claim 1 wherein said wrapping peg includes a plurality of edges adapted to receive a suture.

4. The suture package of claim 1 wherein said wrapping peg includes a plurality of rounded edges adapted to receive a suture.

5. The suture package of claim 1 wherein said wrapping peg includes a post which is triangular in cross-section in order to define three edges that are adapted to receive a suture.

6. The suture package of claim 1 wherein said needle park includes a first slot that is adapted to retain a suture and a second slot adapted to allow access to the suture retained in the first slot.

7. The suture package of claim 6 wherein said second slot is wider and deeper than said first slot.

8. The suture package of claim 1 wherein said needle park includes a first slot that is adapted to receive a suture and a second slot located at an angle below said first slot and adapted to allow access to the suture retained in the first slot.

9. The suture package of claim 1 wherein the apertures are evenly distributed throughout the panel in a pattern comprising a plurality of aligned vertical columns and horizontal rows.

10. A suture package comprising:
a panel with a multiplicity of apertures;
at least one needle park selectively inserted into the apertures and adapted to secure a suture to the suture package; and
at least one wrapping peg selectively inserted into the apertures and adapted to guide the suture within the suture package, the at least one wrapping peg comprising:
a post having a first end and a second end;
a retaining base having a first side and a second side, the first end of the post being attached to the first side of the retaining base;
a retaining cap attached to the second end of the post; and
a peg mounting lug attached to the second side of the retaining base.

11. A suture package comprising:
a panel with a multiplicity of apertures;
at least one needle park selectively inserted into the apertures and adapted to secure a suture to the suture package; and
at least one wrapping peg selectively inserted into the apertures and adapted to guide the suture within the suture package, with the at least one needle park having:
a needle park body having a top end and a bottom end;
a needle park slot on the top end of the needle park body;
a channel at an angle to the needle slot; and
a needle park mounting lug attached to the bottom end of the needle park body which lug can snugly fit into one of said apertures.

12. The suture package of claim 11 wherein the channel is wider and extends deeper into the needle park body than the needle slot.

13. The suture package of claim 1 including a suture having a needle and a suture thread, with the needle retained in said needle park and said suture thread contacting said peg.

14. The suture package of claim 1 including a suture having a needle and a suture thread with barbs extending from said suture thread, with the needle retained in said needle park and said suture thread contacting said peg.

* * * * *

UNITED STATES PATENT AND TRADEMARK OFFICE
CERTIFICATE OF CORRECTION

PATENT NO.       : 8,459,446 B2
APPLICATION NO. : 12/677505
DATED            : June 11, 2013
INVENTOR(S)      : Martin J. Kozlowski It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 458 days.

Signed and Sealed this
Eighth Day of September, 2015

Michelle K. Lee
*Director of the United States Patent and Trademark Office*